United States Patent [19]

Polak et al.

[11] 4,080,565

[45] Mar. 21, 1978

[54] METHOD FOR MEASURING THE POLARIZATION POTENTIAL OF METAL STRUCTURES LOCATED IN AN AGGRESSIVE MEDIUM IN A CURRENT FIELD AND ARRANGEMENT FOR EXECUTION OF THIS METHOD

[75] Inventors: Josef Polak, Prague; Josef Mrazek, Roudnice nad Labem, both of Czechoslovakia

[73] Assignee: Chemoprojekt, Prague, Czechoslovakia

[21] Appl. No.: 680,709

[22] Filed: Apr. 27, 1976

[30] Foreign Application Priority Data

Apr. 28, 1975 Czechoslovakia .................. 2202/75

[51] Int. Cl.² ........................................... G01N 27/00
[52] U.S. Cl. .............................. 324/71 R; 324/65 CR; 324/54
[58] Field of Search .............. 324/71 R, 71 E, 65 CR, 324/37, 51, 54; 204/19.5 C

[56] References Cited

U.S. PATENT DOCUMENTS

| | | | |
|---|---|---|---|
| 3,649,492 | 3/1972 | Marsh et al. | 324/71 R X |
| 3,661,751 | 5/1972 | Wilson | 324/71 R X |
| 3,716,460 | 2/1973 | Weisstuch et al. | 324/71 R X |
| 3,730,869 | 5/1973 | Wilson | 324/71 R X |
| 3,788,962 | 1/1974 | Frenck | 324/71 E X |

*Primary Examiner*—Rudolph V. Rolinec
*Assistant Examiner*—Vincent J. Sunderdick
*Attorney, Agent, or Firm*—Burgess, Ryan and Wayne

[57] ABSTRACT

A method and apparatus for measuring the polarization potential of anodically protected metal structures in moist soil in a current field utilizes auxiliary electrodes and a reference electrode immersed adjacent the metal structure in the same soil. The auxiliary electrodes are connected to the metal structure, then disconnected, and the electrical potential between the auxiliary electrodes and reference electrode is measured immediately after the disconnection.

14 Claims, 2 Drawing Figures

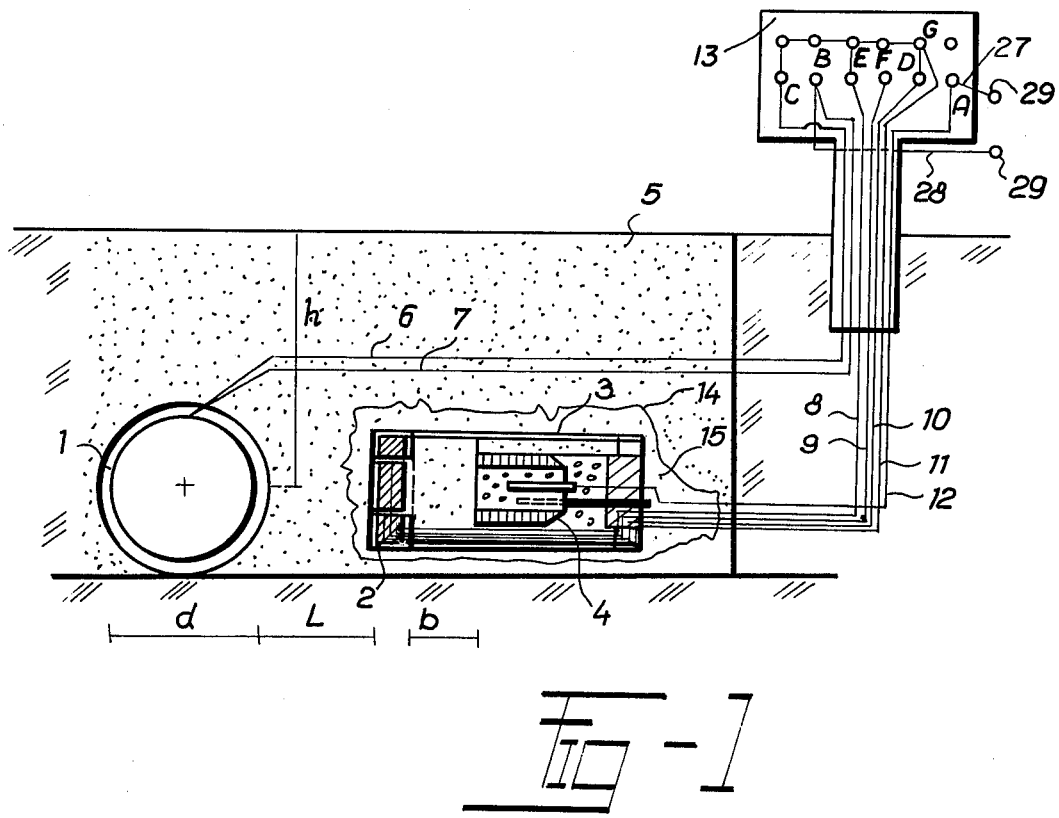
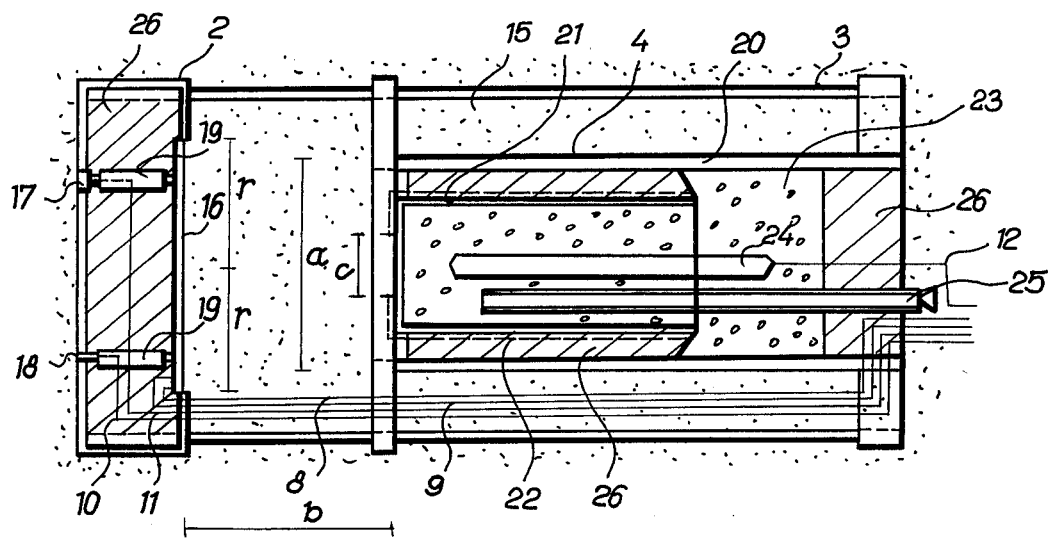

METHOD FOR MEASURING THE POLARIZATION POTENTIAL OF METAL STRUCTURES LOCATED IN AN AGGRESSIVE MEDIUM IN A CURRENT FIELD AND ARRANGEMENT FOR EXECUTION OF THIS METHOD

The invention relates to a method and to an arrangement for measuring the polarization potential of metal structures located in an aggressive medium in a current field generated by an electric current circuit of a cathodic protection or by stray currents and to a method and an arrangement for the control of automatically controlled rectifiers of the cathodic protection. The aggressive medium, for instance soil, where the protected metal structure is embedded acts thereby as electrolyte and causes corrosion of unprotected parts of the structure.

The measurement of the electrolytic potential is the most important measurement for checking the functioning of the cathodic protection and of the conditions of corrosion of a metal structure in places with an aggressive medium and in places where stray DC currents are present. The measured potential is represented by the sum of the following components:

$$U_{on} = U_s + \Delta U_p + \Delta U_{IR} \pm U_d (V) \quad (1)$$

where $U_s$ is the stationary (combined, corrosion) potential (V)

$U_{on}$ is the potential in case current is flowing (the on potential)

$\Delta U_p$ the potential shift due to polarization (due to action of electric current) - the negative polarization shift $\Delta U_{IR}$ the ohmic component of the system structure-electrolyte, the so called pipe to soil potential $U_d$ diffusion potential ± 5 to 38 mV according to the kind of electrolyte soil in dependence on the pH value and on the specific resistance $\rho$.

As the diffusion potential is for a certain pH and $\rho$ of a practically constant value, it can be neglected.

$$U_p = U_s + \Delta U_p \text{ the polarization potential (V)} \quad (2)$$

$U_s \sim U_{off} U_{off}$ is the potential in case current is cut off (off potential)

The ohmic component represents frequently the substantial part of the measured value of the potential. The higher the quality of the insulation coating of the structure, the higher the specific resistance of the aggressive medium (of the soil) and the higher the distance of the electrode from the structure, the higher is the ohmic component. But the ohmic voltage drop does not characterize the corrosion condition of the metal structure. The ohmic component does not show the kinetics of the electrochemical processes proceeding on the metal surface; it does not determine the degree of danger of corrosion or the degree of protection.

The existence of the ohmic component leads in a number of cases to wrong conclusions about corrosion conditions of the structure. A large part of the potential shift can be caused by the ohmic component. The value $U_p$ of the polarization potential is thereby smaller than the value of the minimum protective potential. An arrangement becomes frequently only partly protected, although formally all requirements regarding to maintenance of the protective potential are fulfilled, thereby resulting in a reduction of the lifetime of the arrangement. The degree of protection can be reliably determined solely by the value of the polarization potential of the structure, with elimination of the ohmic component.

Some known methods of measuring the polarization potential with elimination of the ohmic component are based on the principle, that some components of the potential vanish at different speed after cutting off the current.

The ohmic component vanishes approximately after $10^{-8}$ seconds and the electrochemical component (the activating and concentrating polarization) within the range of $10^{-2}$ seconds to several seconds. This enables one to determine the ohmic voltage drop from the changes in the potential with time as the current is cut in and cut off. The first instantaneous voltage drop will correspond to the ohmic component.

Another method applies metal test samples, located in an underground measuring outlet. The method of Pearson is based on the application of a zero circuit, the Holler method on the application of a bridge circuit. These methods have a number of drawbacks. When using methods based on the vanishing of components of the potential at different speeds after cutting off the current, the cutting in and cutting off of places with cathodic protection at long distance pipe lines showed in practice to be not suitable, as it is impossible to cut off at one instant all places, which influence the potential at the measured place, i.e., at the average quality of the insulating coating of the pipe line at least 20 km on both sides of the measured place. In zones with stray currents this method is positively not applicable.

When using the method based on the application of test samples, a substantial drawback is the necessity to provide new underground measuring stations along the pipe line track, thus increasing investment costs and increasing also the number of control measurements in operation. With this arrangement it is also impossible to determine exactly the distance between the portable reference electrode lowered into the measuring station and between the surface of the metal sample, this resulting in certain inaccuracies when determining the voltage drop in the soil surrounding the metal sample.

Further proposed methods such as the zero circuit of Pearson and the bridge circuit of Holler are unsuitable for field measurements as they require special measuring apparatus used in laboratories. These methods for determination of the polarization component of the potential cannot be applied for underground structures in a field of stray currents.

It is an object of this invention to provide a method and an arrangement for measuring the polarization potential of metal structures located in an aggressive medium in a current field, where measurements could be performed for instance on a long distance pipe line without being influenced by the current field due to cathodic protection or due to fields generated by stray currents. It is another object to enable an analysis of the influence of stray currents on the metal structure in the cathodic and anodic zone.

According to this invention the potential difference is measured between a reference electrode and an auxiliary metal electrode immediately after electrically disconnecting the auxiliary metal electrode from the metal structure protected by cathodic protection.

Further advantages and objects of this invention will be apparent from the following description of the method and of the respective arrangement, taken in conjunction with the accompanying drawings, in which:

FIG. 1 shows a polarization potential measurement arrangement according to an embodiment of the present invention; and FIG. 2 is an enlarged more detailed view of a portion of the arrangement shown in FIG. 1.

The following publication, which contains additional explanatory material relating to the present invention, is incorporated into this application by reference and made a part thereof: "Evaluation of Efficiency of Cathodic Protection of Buried Pipelines" by J. Polak, M.E., Chemoprojekt, Czechoslovakia, Paper F4, First International Conference on the Internal and External Protection of Pipes - Sept. 9-11, 1975, University of Durham, Organized and Sponsored by BHRA Fluid Engineering, Copyright BHRA Fluid Engineering, Cranfield, Bedford, England.

The arrangement according to this invention comprises a replaceable panel containing at least a single auxiliary electrode, this panel being fixed to a skeleton structure of electrically nonconductive material supporting a reference electrode, whereby the panel fixed to the skeleton structure is situated in the same aggressive medium as the protected metal structure at a distance "L" from this structure, measured from the insulated surface of the metal structure in a plane perpendicular to the longitudinal axis of the protected structure, whereby the metal structure, the reference electrode and the auxiliary metal electrode or auxiliary electrodes are connected by conductors to terminals of a measuring device on the surface.

From the point of view of determination of conditions of corrosion and of the efficiency of electrochemical protection of insulated structures it is necessary to determine the extent and shape of faults in the insulation of surfaces of exposed metal and the values of the polarization potential $U_p$ at places where the insulation is damaged. It can be generally said, that the exposed places will have the shape of curved surfaces (e.g. for a pipe line or, for underground cylindrical tanks). In order to derive the necessary relations, extreme shapes should be considered: a circular plate on one side for small faults in insulation and for a current field in the neighborhood of the fault; a hemisphere for large faults in insulation and for a current field at a greater distance from the place of the fault, for instance on the surface of the soil. From the point of view of technology a plate electrode can be advantageously used for the pick-up device of the polarization potential, where faults in insulation including the adjacent insulating coating are simulated.

From the point of view of a uniform distribution of the current field in the neighborhood of the metal electrode and the simpler mathematic relations resulting therefrom, it would be suitable to use for the auxiliary metal electrode the shape of a hemisphere. In case of equal surfaces of the circular plate and of the hemisphere, the current density of the hemisphere is 11% higher than that of the circular plate; the proper insulation fault will therefore be within an acceptable tolerance of about 5%. A non uniform distribution of the density of the protecting current is experienced when using a circular plate. The equipotential lines have the shape of a flattened ellipsoid. The highest density of the protecting current is on the borders, the lowest in the middle of the plate. These circumstances have to be taken into account in the design of the pick-up device for polarization potentials; the stable reference electrode must be situated at such a distance from the auxiliary metal electrode to measure the mean value of the potential including the ohmic component in a layer "b" of the aggressive medium "b" representing the perpendicular distance between the nearest place of the metal electrode and the measuring surface of the stable reference electrode.

This distance "b" must be such that the current density at the surface of the metal electrode attains at least 95% of the value it would have in a case where the stable reference electrode is not situated close to the metal electrode.

As the area "S" of a circular plate $S = \pi r^2$ (where "r" is the radius of the plate) is smaller than the area "$S_T$" of a voltage funnel in a section at a perpendicular distance "b" from the plate at the place of the mesuring surface of the stable referrence electrode, the relation $S_T = f(b)$ is determined with repect to the arrangement of equipotential lines as follows: From equations No. 1 and 2 follows:

$$U_{on} = U_p + \Delta U_{IR} \ (V) \tag{3}$$

where $U_{on}$ is the potential with the cathodic protection switched on.

If $\Delta U_p$ is relatively stable and if the reading is accomplished within 2 seconds after cutting off $$U_p = U_{off}(V) \tag{4}$$

where $U_{off}$ is the potential immediately after cutting off the cathodic protection.

Equation No. 3 can be therefore written as follows:

$$U_{on} = U_{off} + \frac{I \cdot B \cdot \rho}{S_T} \quad (V) \tag{5}$$

as the current density $$j = \frac{E}{\rho} \quad \frac{A}{m^2} \tag{6}$$

where E is the intensity of the current field V/m (volts/meter)

ρ the specific resistance of the electrolyte (of the aggressive medium) ω/m

Equation 6 can be transcribed $$j \cdot b = \frac{E \cdot b}{\rho} \text{ or } j \cdot b \cdot \rho = E \cdot b \tag{7}$$

Finally equation 7 can be adjusted $$\frac{I}{S_T} \cdot b \cdot \rho = E \cdot b = \Delta U_{IR} \quad (V) \tag{8}$$

From equation 5 can be determined $$S_T = \frac{I \cdot b \, \rho}{U_{on} - U_{off}} \quad m^2 \tag{9}$$

The value $S_T$ is for a certain "ρ" and "b" and depth of embedding under the surface of the soil practically constant and it is therefore possible to determine from equations No. 4 and 5 $U_p$ for different values of $U_{on}$, I, where I is the electric current flowing from the auxiliary metal electrode to the metal structure in A, or in the opposite direction in the anodic zone with stray currents.

We have found, that the most advantageous arrangement according to this invention is where the replaceable panel contains three auxiliary metal electrodes made of the same material as the protected metal structure.

The auxiliary metal electrodes have the shape of circular plates with areas S, S.$10^{-2}$, and S. $10^{-4}$. The auxiliary circular metal electrode with the area S is in the panel situated on a side, facing the stable reference electrode at a perpendicular distance "$b$" corresponding to conditions $b \geqq 0,866r$ and $b \geqq 0, 5a$, where "$r$" is the radius of the circular auxiliary electrode having an area of S and "$a$" is the external diameter of the stable reference electrode. The auxiliary metal electrodes with areas S.$10^{-2}$ and S. $10^{-4}$ are situated in the replaceable panel on its side facing the protected metal structure. The stable reference electrode situated in the skeleton structure of non-metallic material comprises a cylinder of copper of a purity of 99.9% immersed in a porous vessel, provided with an insulating coating and filled with a mixture of crystallized copper sulphate and sawdust. The content just prior to installing is potted with a solution of copper sulphate and sealed by cast resin and by some casting material. Rather important is the selection of the diameter of the measuring area of the stable reference electrode, determined by the part thereof free of insulating coating facing the stable metal electrode. In case of a small diameter of this area, the transistory resistance of the electrode is too high (higher than 1000 $\omega$,), thus influencing the accuracy of measurements; in case of a large diameter there is an increased danger of trickling of the copper sulphate from the reference electrode and of a contamination of the natural aggressive medium.

We have found, that the optimum diameter "$c$" of the circular measuring area of the stable reference electrode is within the limits 100mm $> c >$ 20mm. The possible trickling of the solution of copper sulphate is practically prevented by the above described kind of arrangement.

For arenaceous-agrillaceous and arenaceous soils it is necessary for the prevention of diffusion of copper sulphate to the metal electrode to provide in close proximity to the porous surface of the stable reference electrode a layer of clay, for instance of bentonite, of a thickness about on the order of 3cm.

The electrodes are fixed in the exchangeable panel by electrode holders and are sealed by some casting material and cast resin. All conductors from the electrodes ar disposed in a common cable joint, sealed by a casting material, connected to a common cable, leading to terminals of apparatus of a measuring device on the surface. The skeleton structure with the stable reference electrode and with the exchangeable panel containing the electrodes is inserted into a wrapping of textile material, for instance into a jute bag, filled with sieved soil sprayed with water prior to embedding.

The method and arrangement according to this invention have a number of advantages.

An advantage of this arrangement is that it can be situated quite close to the metal structure, whereby the measuring of the polarization potential is not influenced by the current field of this metal structure. With the method according to this invention it is possible after disconnecting the auxiliary metal electrodes in the measuring device from the metal structure, for instance from a long distance pipe line, to measure the value of the polarization potential $U_p$ by means of a stable reference electrode without being influenced by the current field due to operation of the cathodic protection or by a field generated by stray currents. With the value of the ohmic component of the potential in the layer "$b$" of the potential pick-up device known, it is possible to analyze in detail the influence of stray currents on the metal structure in the cathodic and anodic zone, such analysis being impossible with previously known methods.

The arrangement can be advantageously embedded together with a new pipe line into the same ditch at places where measuring devices are arranged and where the kind of soil (its specific resistance) is changing and at places of supposed anodic and cathodic zones in places with stray currents. In zones with alternating polarity the surface of the auxiliary metal electrode is polarized to a mean value corresponding to the condition and quaity of protection of the investigated zone and this value can be measured after disconnecting the electrodes from the pipe line.

When using auxiliary metal electrodes with areas S, S.$10^{-2}$ and S.$10^{-4}$ it is possible to consider the possiblity of changing the polarity with the thus resulting consequences due to the increase of current density for a unit area at smaller areas, said consequences being for instance a fault of the insulating coating, increased generation of alkaline substances or increased generation of hydrogen, causing a danger of corrosion ruptures, particularly at pipe lines stressed by heat or pressure, as for instance high pressure gas pipe lines. If an excessive polarization is determined in time by the method and arrangement according to this invention it is possible to prevent dangerous situations by proper intervention.

The arrangement according to this invention can be advantageously applied for newly built steel pipe lines provided with cathodic protection or exposed to the action of stray currents. It can be, however, also applied for existing pipe lines for gas and other products, where there are strict requirements for safety of operation of the pipe line at places where measuring devices are provided and in places where changes of the aggressive medium (of the soil) are observed. The auxiliary metal electrodes of different known areas embedded at a known depth can serve as comparison standard for a quantitative evaluation of faults of the insulation determined by the Pearson method and for judging the danger of cracking of pipe lines stressed by heat and pressure at given conditions due to corrosion.

The method and arrangement according to this invention can be also advantageously used in places where stray currents are observed even if it is additionally installed. The terminals of the measuring device are connected by cables to terminals for picking-up potentials for a contactless regulator for the control of a station for cathodic protection.

The arrangement according to this invention can be also applied for structures of more limited length than pipelines, as are for instance storage tanks, for determination of the polarization potential $U_p$ of places accessible only with difficulty from the surface, which potential is frequently distorted for instance by the current field of the ground system. It is also possible to simulate on the auxiliary metal electrode of the arrangement an imperfectly applied insulating condition and to determine the degree of electrochemical protection under given conditions. The arrangement can be also applied for determination of the polarization potential of metal sheetings of cables.

At places where the cathodically protected line structures is crossing with another metal structure it is possible to utilize the arrangement for determination of the interference effects and of the density of the interference current, i.e., of the corrosion current between auxiliary metal electrodes of different areas, simulating a damaged insulation condition, and between the other structures, by connecting the measuring terminals of the control device to a millivoltmeter. It is finally possible to utilize the arrangement of checking the function of insulating joints and for determining the transistory resistance of the system pipe line protection.

The drawing shows an outline of an embodiment of this invention where FIG. 1 is a vertical sectional view of the arrangement perpendicularly to the longitudinal axis of the protected metal structure; FIG. 2 is a similar enlarged view of the proper arrangement.

FIG. 1 shows in cross section a protected metal structure, an insulated steel pipe line 1, embedded at a depth "$h$" in an aggressive medium 5, the depth "$h$" measured from the surface of the soil to the longitudinal axis of the pipe line 1. The arrangement according to the invention, comprising a replaceable panel 2 with three auxiliary electrodes 16, 17, 18, is situated at the distance "$L$", equal in this exemplary embodiment to the external diameter "$d$" of the pipe line including the insulation - in the case given $d = 320$mm. As more clearly shown in FIG. 2, the replaceable panel 2 with electrodes 16, 17, 18 is fixed to a skeleton structure 3 of electrically non-conductive material, for instance of polyvinyl chloride, within which structure a stable reference electrode 24 is provided. The skeleton structure 3 together with the stable reference electrode 24 and the exchangeable panel 2 supporting auxiliary steel electrodes 16, 17, 18, (which panel is made as a standard component of skeleton structure 3), is inserted in a jute bag 14 filled with screened soil 15 from the place where the pipe line is located and soaked with water prior to embedding the arrangement according to this invention into the ditch. The protected insulated steel pipe line 1 is connected with the apparatus terminals B, and C of a measuring device 13 by cables 6, 7 respectively. The auxiliary metal electrode 16 is connected to apparatus terminals E and F of the measuring device 13 by conductors 8 and, 9 respectively. The auxiliary electrode 18 is connected to terminal D of the measuring device 13 by conductor 10. The auxiliary electrode 17 is connected to an apparatus termial G of the measuring device 13 by conductor 11 and the stable reference electrode 24 is connected to terminal A of measuring device 13 by conductor 12. The terminals A, B of the measuring device 13 are connected by conductors 27 and 28 to terminals 29 for picking up the potential for use by an automatic contactless regulator of the station for cathodic protection.

FIG. 2 shows the arrangement according to this invention in more detail equally in a cross section perpendicularly to the longitudinal axis of the protected pipeline 1. The respective arrangement according to this invention is in the case given of a length of about 400 to 500mm, so that it can be embedded into a common ditch with the pipe line 1 after some widening of the ditch. Auxiliary steel electrodes 16, 17 and 18 in the shape of circular plates are fixed on the exchangeable panel 2 by holders 19 of non-metallic material. The auxiliary electrode 16 has an overall measuring area $S = 100$ cm² and is on the replaceable panel 2 situated opposite to the stable reference electrode 24 at a perpendicular distance "$b$". In the case given the minimum distance $b = 0.866 \times 56.5 = 49.0$ mm, $b = 0.5 \times 90 = 45.0$mm, i.e. approximately 50mm. In that case the optimum distance was between 50 and 100 mm, i.e. about 75 mm.

The auxiliary electrode 17 has an overall measuring area $S.10^{-2} = 1$ cm² and the electrode 18 a measuring area $S.10^{-4} = 1$ mm². Electrodes 17 and 18 are fixed on the replaceable panel 2 opposite to the protected pipe line 1. The electrodes are in the panel 2 sealed by cast resin 26. In adition to the replaceable panel 2 a stable reference electrode 24 within a tube 20 of PVC of an external diameter "$a$" = 90mm is fixed on the skeleton structue 3. The stable reference electrode 24 comprises a cylinder of a length of 100 to 150 mm and a diameter 10 mm of pure copper of a purity at least 99.9%, immersed in a porous vessel 21 provided with an insulating coating 22 of laminated resin and containing a filling of a mixture of crystals of copper sulphate and sawdust, which filling has been soaked prior to embedding into the ditch with an aqueous solution of copper sulphate by means of a perforated tube 25. On the surface of the porous vessel 21 facing the replaceable panel 2 a circular measuring surface of a diameter "$c$" is left without the insulating coating 22. The reference electrode 24 is in the tube 20 sealed by cast resin 26. The diameter "$c$" of the measuring surface of the stable reference electrode 24 is for said embodiment equal to 38 mm corresponding to the relation 100mm $> c >$ 20mm.

Using the measuring device 13, the polarization potential of each of the auxiliary electrodes 16, 17 and 18 with respect to the adjacent earth is measured as follows.

The unit 3 is buried in the ground within the sack 14 as previously described, adjacent the pipeline 1, and thereby becomes galvanically coupled to said pipeline by way of the earth, which acts as an electrolyte. The unit 3 is allowed to remain undisturbed for at least ten days prior to the measuring process.

The switch connections within the device 13 are established so that the pipeline-connected terminal C is connected to the terminals D, E and G, which in turn are electrically connected to the auxiliary electrodes 18, 16 and 17 respectively. The switch connections are then changed so that the pipeline-connected terminal C is no longer electrically connected to the auxiliary electrode terminals D, E and G and these terminals are no longer connected to each other.

Within two to three seconds after the pipeline connected terminal C is electrically disconnected from the auxiliary electrode terminals D, E and G, the potential difference between the reference electrode connected terminal A and a selected one of the auxiliary electrode connected terminals D, E and G is measured by means of a high impedance millivoltmeter. A DC millivoltmeter is used with its positive terminal connected to terminal A and its negative terminal connected to terminal D, E or G.

The reading of the millivoltmeter then corresponds to the polarization potential between the auxiliary electrode and the earth.

The aforementioned process may be repeated to measure the polarization potential between the remaining auxiliary electrodes (one by one) and the earth.

Thus, current may be provided and removed by a current source in measuring device 13. Furthermore, according to the method immediately after the removal of current provided through terminal C in FIG. 1 a high resistance volt meter connected between terminals A and D of measuring device 13 provides the polarization potential measurement previously described. Furthermore, a milliammeter in measuring device 13 connected between terminals 1C and 1E makes it possible to derive the current density of the anodic protection device.

What is claimed is:

1. A method for measuring the effect of a current field on a holiday in the coating of an insulated protected metal structure by measuring the polarization potential of said metal structure, said structure being located in an aggressive medium in a current field, comprising placing an auxiliary metal electrode, simulating a holiday in the coating of the protected metal structure, in the aggressive medium near the metal structure, placing a reference electrode near the auxiliary electrode, connecting the auxiliary electrode to the protected metal structure to polarize said auxiliary electrode, disconnecting the polarized auxiliary metal electrode from the protected metal structure after the step of connecting the auxiliary metal electrode, and measuring the potential difference between the polarized auxiliary electrode and the reference electrode immediately after said step of disconnecting said polarized auxiliary electrode.

2. Arrangement for measuring the polarization potential of metal structures located in an aggressive medium in a current field, comprising a skeleton structure of electrically non-conductive material, a stable reference electrode affixed to and supported by said skeleton structure, an exchangeable panel affixed to and supported by said skeleton structure, at least one auxiliary metal electrode on said exchangeable panel, the skeleton structure with the stable reference electrode and the exchangeable panel being embedded in the same aggressive medium in the electrical field as the protected metal structure at a mutual distance "L" measured in a plane perpendicular to a longitudinal axis of the protected metal structure including its insulating coating, cables connected to the protected metal structure, conductors connected to the auxiliary metal electrode, a conductor connected to the stable reference electrode, a potential measuring device, and means connecting the cables and the conductors of the auxiliary and reference electrodes to said potential measuring device.

3. Arrangement as in claim 2, wherein the exchangeable panel is provided with three auxiliary metal electrodes.

4. Arrangement as in claim 2 wherein the skeleton structure supporting the stable reference electrode and the exchangeable panel with at least a sngle auxiliary metal electrode are inserted into a textile covering with a filling of screened soil from the place where the arrangement is embedded.

5. Arrangement as in claim 2, wherein the auxiliary metal electrodes are of the same metal as in the protected metal structure, the auxiliary metal electrodes having a bare surface, said bare surface being in direct contact with the aggressive medium, by way of a simulated defective insulation.

6. Arrangement as in claim 2, wherein the exchangeable panel supporting auxiliary metal electrodes arranged as a standard unit of the skeleton structure and containing electrode holders of electrically non-conductive material for said auxiliary metal electrodes and sealing means of cast resin.

7. Arrangement as in claim 3, with a skeleton structure supporting a stable reference electrode having an overall external diameter "$a$" and a measuring surface of a diameter "$c$", and wherein said exchangeable panel is provided with three auxiliary metal electrodes, a first auxiliary metal electrode fixed on this panel at its side facing the measuring surface of the stable reference electrode at a distance "$b$" from this electrode, the measuring surface of this first auxiliary metal electrode having an area "$S$", a second and a third auxiliary metal electrode provided on the exchangeable panel on the side facing the protected metal structure, said second and third auxiliary metal electrodes having measuring areas of $S.10^{-2}$ and $S.10^{-4}$ respectively.

8. Arrangement as in claim 2, wherein the auxiliary metal electrodes have the shape of circular plates.

9. Arrangement as in claim 8, wherein these circular plates being insulated on one side.

10. Arrangement as in claim 2, wherein the stable reference electrode is supported by the skeleton structure at the distance "$b$" from the first auxiliary electrode with a measuring area "$S$" arranged on skeleton structure coaxially therewith, the stable reference electrode comprising a cylinder of pure copper of a purity at least 99.9% situated in a porous vessel provided with an insulating coating leaving at the surface facing the said first auxiliary metal electrode a bare measuring surface, the porous vessel having a filling of a mixture of crystals of copper sulphate, the porous vessel inserted in a protecting tube of an external diameter "$a$" and sealed therein by cast resin.

11. Arrangement as in claim 2, wherein a perpendicular distance "$b$" between the measuring surface of the stable reference electrode and between the measuring surface of the first auxiliary metal electrode with a surface area "$S$" complying with the relations $b \geq 0.866r$ and $b \geq 0.5a$, where "$r$" is the radius of the circular surface of the first auxiliary metal electrode with a measuring area "$S$", and "$a$" is the external diameter of the protecting tube of the stable reference electrode, whereby the stable reference electrode is arranged in axial relation with respect to the auxiliary metal electrode.

12. Arrangement as in claim 2, wherein a perpendicular distance "L" between surfaces of the second and third auxiliary metal electrodes with measuring areas $S.10^{-2}$ and $S.10^{-4}$ respectively, supported by the exchangeable panel and between the protected metal structure complies with the relations $L \geq d$ and $L \geq 2h$, where "$d$" is the external diameter of the protected metal structure including its insulating coating and "$h$" the depth at which the protected metal structure is embedded below the surface of the aggressive medium, measured to the longitudinal axis of the protected metal structure.

13. Arrangement as in claim 2, wherein a diameter "$c$" of the measuring surface of the stable reference electrode supported by the skeleton structure complies with the relation 100mm$>c>$20mm.

14. Arrangement as in claim 2, with apparatus terminals of the measuring device on the surface connected by conductors with terminals for picking-up potentials of an automatic contactless regulator of a controlled station of cathodic protection.

* * * * *

UNITED STATES PATENT OFFICE
CERTIFICATE OF CORRECTION

Patent No. 4,080,565      Dated March 21, 1978

Inventor(s) Josef Polak, et al

It is certified that error appears in the above-identified patent and that said Letters Patent are hereby corrected as shown below:

Column 5, line 53:    "ar" should be --are--.

Column 7, line 44:    "with the" should be --to--;

"B," should be --B--.

line 45:    "6,7" should be --6 and 7--.

line 47:    "and," should be --and--.

Column 9, line 54:    "sngle" should be --single--.

IN THE ABSTRACT:

line 2, "anodically" should read --cathodically--

Signed and Sealed this

*Fourteenth* Day of *November 1978*

[SEAL]

*Attest:*

RUTH C. MASON
*Attesting Officer*

DONALD W. BANNER
*Commissioner of Patents and Trademarks*